United States Patent [19]

Shimizu

[11] Patent Number: 5,311,658
[45] Date of Patent: May 17, 1994

[54] APPARATUS FOR PRODUCING LIVING BODY LEADING ELECTRODE

[75] Inventor: Chuji Shimizu, Tokyo, Japan

[73] Assignee: Fukuda Denshi Co., Ltd., Tokyo, Japan

[21] Appl. No.: 933,071

[22] Filed: Aug. 21, 1992

[30] Foreign Application Priority Data

Apr. 6, 1992 [JP] Japan ................... 4-113031

[51] Int. Cl.⁵ ...................... B23P 19/04; H01R 43/00
[52] U.S. Cl. ......................................... 29/746; 29/877
[58] Field of Search ............... 29/874, 877, 878, 882, 29/825, 745–748, 811.2, 812, 881, 884; 128/640, 798, 802, 641; 252/500; 606/32

[56] References Cited

U.S. PATENT DOCUMENTS

| | | | |
|---|---|---|---|
| 4,063,352 | 12/1977 | Bevilacqua | 29/877 |
| 4,114,263 | 9/1978 | Szpur | 29/877 |
| 4,317,278 | 3/1982 | Carmon et al. | 29/874 X |
| 4,362,165 | 12/1982 | Carmon et al. | 128/640 |
| 4,393,584 | 7/1983 | Bare et al. | 29/877 |
| 4,433,481 | 2/1984 | Szpur | 29/878 |
| 4,515,162 | 5/1985 | Yamamoto et al. | 128/640 |
| 4,524,775 | 6/1985 | Rasmussen | 29/882 X |
| 4,721,111 | 1/1988 | Muttitt | 29/877 X |
| 4,979,517 | 12/1990 | Grossman et al. | 128/798 |
| 5,024,227 | 6/1991 | Schmid | 128/640 |

FOREIGN PATENT DOCUMENTS 49539 2/1989 Japan ................... 128/640

Primary Examiner—Peter Dungba Vo
Attorney, Agent, or Firm—Sughrue, Mion, Zinn, Macpeak & Seas

[57] ABSTRACT

An apparatus for producing a living body leading electrode includes a first substrate 10 to which first boards 1 are fixed in a plurality of rows. A plurality of skin adhering members 101 with openings 102 are bonded to the first boards. A second substrate 20 is provided to which second boards 2 are fixed in a plurality of rows corresponding to the first boards 1. A plurality of electrode elements 103 are placed on the second boards 2. A pouring means 30 is provided for pouring a solution of electrolyte 100 into the upper portions of the openings 102 formed on the skin adhering members 101. A hardening device 40 for hardening the poured solution of electrolyte 100, thereby fixing the side faces 100A of the electrolyte 100 to the side walls 102A of the openings 102, which first substrate 10 and second substrate 20 may be superposed on each other.

3 Claims, 5 Drawing Sheets

APPARATUS FOR PRODUCING LIVING BODY LEADING ELECTRODE

BACKGROUND OF THE INVENTION

1. Field of the Invention

The present invention relates to an apparatus for producing an electrode for leading an electrocardiogram signal from the living body.

More particularly, it relates to an apparatus for producing a living body leading electrode which is mounted on the breast of a patient with heart disease in case of leading an electrocardiogram signal from the living body of the patient.

2. Description of the Related Art

Conventionally, an electrode as shown in FIGS. 1A to 1C has been taken as an example of a living body leading electrode mounted on the breast of a patient with heart disease.

In these drawings, reference numeral 1000 is an electrolyte, 1001 a member for adhering the electrode to the skin of the breast of the patient, 1002 an opening, 1003 an electrode element, 1004 a lead wire, and 1005 a member for supporting the electrode element.

The electrode element 1003 is mounted on the central portion of the electrode element supporting member 1005, and the skin adhering member 1001 stuck so as to surround it.

The opening 1002 is formed in the skin adhering member 1001 as shown in FIG. 1A, through which opening 1002 the electrolyte 1000 is placed on the electrode element 1003, and is connected with it electrically.

When the electrode as shown in FIG. 1A is used, the skin adhering member 1001 is contacted with the breast of the patient.

Accordingly, an electrocardiogram signal led through the electrolyte 1000 and the electrode element 1003 is transmitted in the lead wire 1004, inputted into an electrocardiograph where the electrocardiogram signal is analyzed in the required way.

However, the problems of the prior art as shown in FIG. 1A are as follows.

(1) When the electrode is mounted on the breast of the patient, the electrolyte 1000 comes off the electrode easily and remains on the skin.

In the prior art, as shown with an arrow a of FIG. 1A, the electrolyte 1000, in a solid state, is merely placed on the electrode element 1003 through the opening 1002.

Hence, since a gap S is formed between the electrolyte 1000 and the opening 1002 as shown in FIG. 1B, the two are not contacted with each other.

Accordingly, after an electrocardiogram signal is led by bonding the electrode on the breast of the patient, in case of removing it from the breast, the electrolyte 1000 is separated from the electrode, and consequently it remains on the breast.

(2) The efficiency of producing the electrode is low.

As aforementioned, in the prior art, the electrolyte 1000 in a solid state is placed on the electrode element 1003 through the opening 1002.

In this case, each electrolyte 1000 must be picked up one by one with a pincette, thereby it is placed on the electrode element 1003.

And, each electrolyte 1000 is formed by punching an electrolyte 2000 in a solid state as shown in FIG. 1C.

Hence, for this sake, a punching process is necessary.

Moreover, in the punching process, all of the electrolyte 2000 is not used, but the part remaining after the electrolytes 1000 have been punched is wasted as shown with an oblique line, which results in a great loss.

Consequently, the prior art has the problems as follows.

That is to say, a process for punching the electrolyte 1000 is necessary, in which process there is the wasted portion, and a great loss.

Moreover, it is necessary to add the step in that the electrolyte 1000 must be picked up one by one with a pincette, and thereafter it is placed on the electrode element 1003.

Accordingly, the efficiency of producing the electrode is extremely low.

SUMMARY OF THE INVENTION

An object of the present invention is to prevent the electrolyte from being separated in case of removing the living body leading electrode from the breast, and to elevate the efficiency of producing the living body leading electrode.

The above-mentioned object can be achieved by a living body leading electrode comprising an electrode element 103 placed at about the central portion of an electrode element supporting member 105. An annular skin adhering member 101 is bonded to the surrounding portion of the electrode element supporting member 105. An electrolyte 100 is inserted into an opening 102 of the skin adhering member 101. The electrolyte 100 is connected electrically with the electrode element 103, the side face 100A of which electrolyte 100 is fixed to the side wall 102A of the opening 102.

A method for producing a living body leading electrode comprises a first step (A) wherein a plurality of annular skin adhering members 101 are bonded to a first board I, a solution of electrolyte 100 is poured into the upper portions of openings 102 of the skin adhering members 101 and is hardened. The side faces 100A of the electrolytes 100 are fixed to the side walls 102A of said openings 102. The method further comprises a second step (B), wherein a plurality of electrode elements 103 are placed on a second board 2, corresponding to a plurality of said electrolytes 100 on said first board 1, and a third step (C) wherein the side of said first board 1, where said skin adhering members 101 and said electrolytes 100 are placed, and the side of said second board 2, where said electrode elements 103 are placed, are disposed in opposing relationship, thereafter said first board 1 and said second board 2 are superposed.

Further, an apparatus for producing a living body leading electrode comprising a first substrate 10 to which first boards 1 are fixed in a plurality of rows, to which first boards 1 a plurality of skin adhering members 101 with openings 102 are bonded, a second substrate 20 to which second boards 2 are fixed in a plurality of rows, corresponding to the first boards 1, on which second boards 2 a plurality of electrode elements 103 are placed, a pouring means 30 for pouring solutions of electrolytes 100 into the upper portions of said openings 102 formed on said skin adhering members 101 bonded to said first boards 1 fixed to said first substrate 10, and a hardening means 40 for hardening said poured solutions of electrolyte 100, thereby fixing the side faces 100A of said electrolyte 100 to the side walls 102A of said openings 102, which first substrate 10 and second substrate 20 may be superposed on each other.

BRIEF DESCRIPTION OF THE DRAWINGS

Further features and advantages of the present invention will be apparent from the ensuing description with reference to the accompanying drawings, wherein:

DESCRIPTION OF THE PREFERRED EMBODIMENTS (1) A living body leading electrode to be produced with an apparatus in accordance with the present invention FIGS. 2A to 2D are drawings of an embodiment of a living body leading electrode to be produced with an apparatus in accordance with the present invention, wherein reference numeral 100 shows an electrolyte, 101 a member for adhering the electrolyte 100 to the skin of the breast of a patient with heart disease, 102 an opening, 103 an electrode element, and 105 a member for supporting the electrode element 103.

The member 105 for supporting the electrode element 103 is shaped by a disk made of synthetic paper, on the central portion of which member 105 the electrode element 103 is placed.

Figure 3:
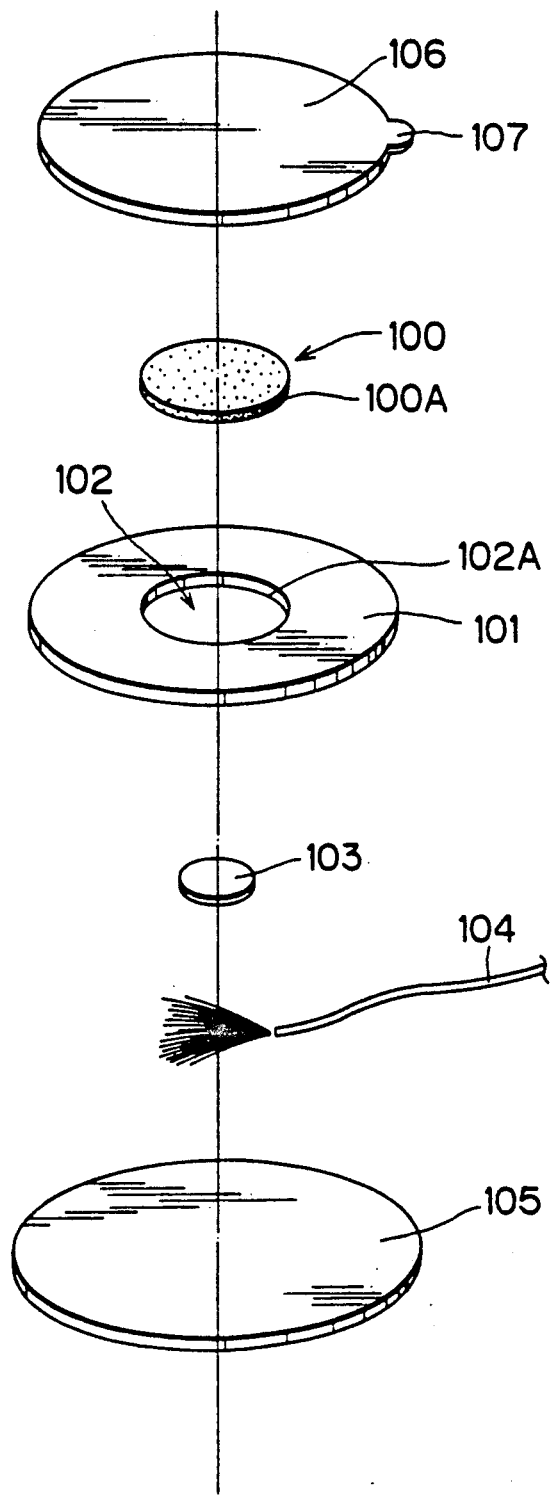
FIG. 3 is a drawing of another embodiment of a living body leading electrode to be produced with an apparatus in accordance with the present invention.

In this embodiment, the explanation refers to a carbon type electrode as shown in FIG. 3, wherein a lead wire 104 is connected with the electrode element 103.

The lead wire 104 and the electrode element 103 are both made from carbon fiber.

An electrocardiogram signal led through this electrode element 103 and the electrolyte 100 is transmitted in the lead wire 104, input into an electrocardiograph connected with the lead wire 104, in which electrocardiograph it is analyzed in the predetermined way.

As shown in FIG. 3, the electrode element 103 is placed on carbon wires in a spread or fanned state projected from the end of the lead wire 104.

Figure 1A:
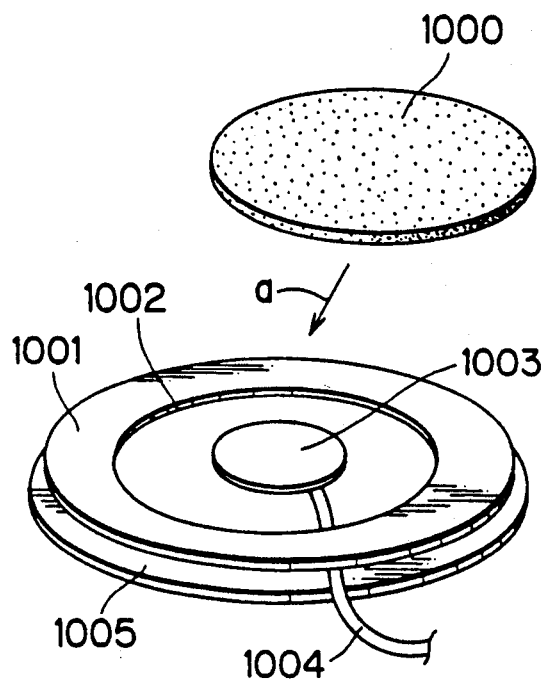
FIGS. 1A to 1C are explanatory drawings of the prior art.
Figure 1B:
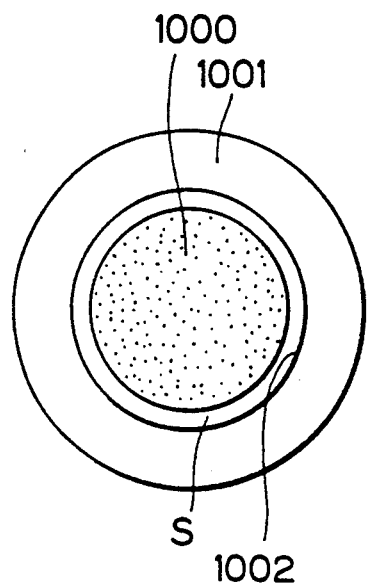
Figure 1C:
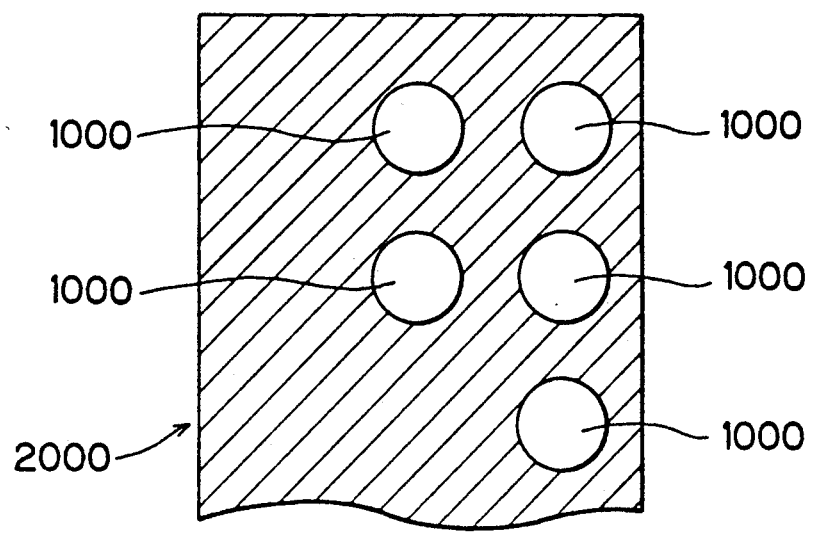
Figure 2A:
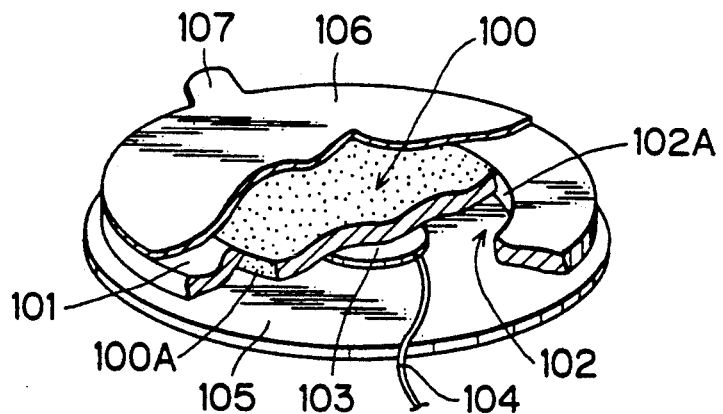
FIGS. 2A to 2D are drawings of an embodiment of a living body leading electrode to be produced with an apparatus in accordance with the present invention.

An annular member 101 for adhering the electrode to the skin is bonded on the surrounding portion of the member 105 for supporting the electrode element as shown in FIG. 2A, which member 101 is contacted with the breast of the patient.

The skin adhering member 101 is made from a foamed member of polybutadiene or polyolefin etc., on both the front and back surfaces of which skin adhering member 101 adhesion treatment is carried out.

A circular opening 102 is formed in the skin adhering member 101, to which skin adhering member 101 a protection sheet 106 is adhered so as to cover the opening 102, which protection sheet 106 is taken off by handling a grip 107 with a users fingers in case of using the living body leading electrode in accordance with the present invention.

Moreover, the electrolyte 100 connected with the electrode element 103 is inserted in the opening 102, the side face 100A of which electrolyte 100 is fixed to the side wall 102A of the opening 102.

Figure 2B:
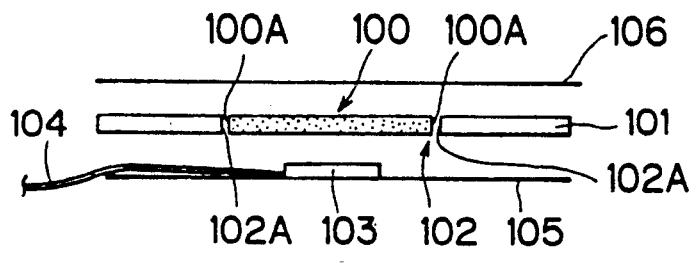

That is to say, in the opening 102, the electrolyte 100 is placed on the electrode element supporting member 105 and the electrode element 103, as well as the side face 100A of it is fixed to the side wall 102A of the opening 102, as shown in FIG. 2B.

Figure 2C:
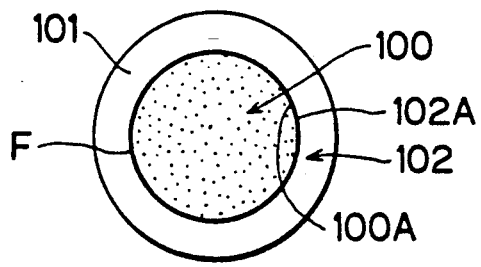

Hence, as shown with a thick line F in FIG. 2C, there is no space between the electrolyte 100 and the opening 102, the two being in contact with each other.

Accordingly, when the living body leading electrode in accordance with the present invention is removed from the breast, the electrolyte 100 is removed together with the skin adhering member 101, only the electrolyte 100 does not remain on the breast.

The electrolyte 100 has conductive and adhesive characteristics, and is broadly divided into an electrolyte in a sol state and an electrolyte in a gel state.

Figure 2D:
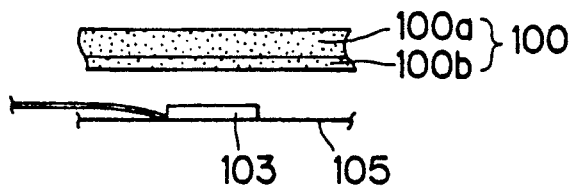

This electrolyte 100 may be formed by laying an electrolyte 100a in a gel state on top of an electrolyte 100b in a sol state, as shown in FIG. 2D.

This is because, as is well known, the impedance between the skin surface of the breast of the patient and the electrode element 103 is made lower and that noise superimposed on an electrocardiogram signal is decreased by stabilizing polarization voltage for a short time, which polarization voltage is a counter electromotive force provided in the direction inverse to that of a living body current flowing to the electrode element 103 from the skin surface of the breast of the patient.

(2) A method to be carried out by using an apparatus in accordance with the present invention.

Figure 4A:
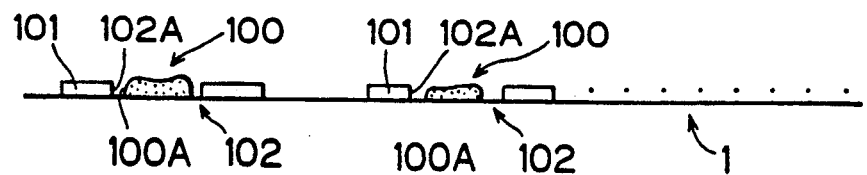
FIGS. 4A to 4C are drawings of an embodiment of a method to be carried out by using an apparatus in accordance with the present invention.
Figure 4B:
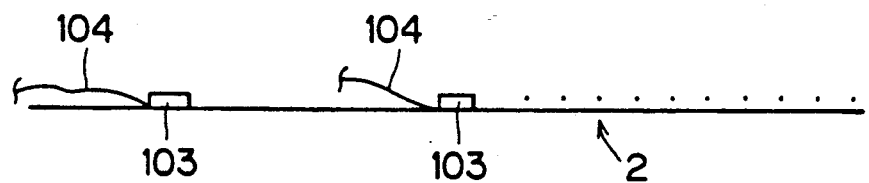
Figure 4C:
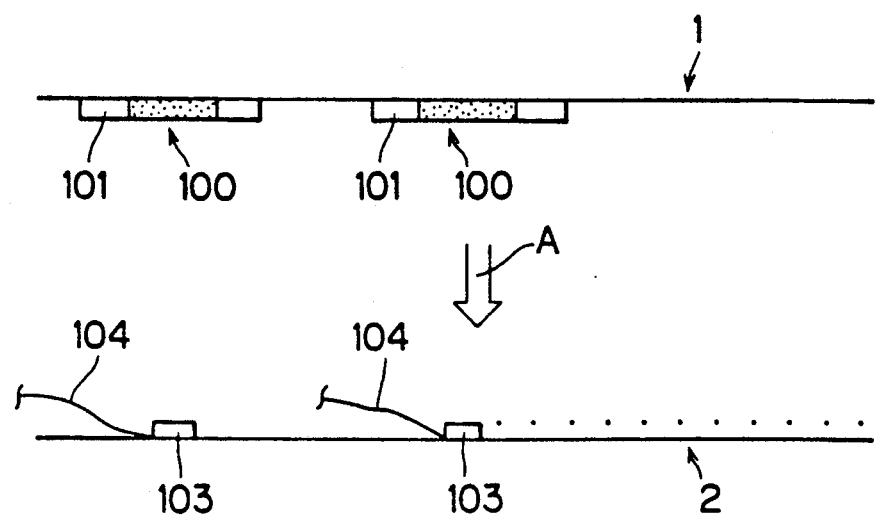

FIGS. 4A to 4C are drawings of an embodiment of a method to be carried out by using an apparatus in accordance with the present invention.

(i) The first step (A)

In the first step (A), as shown in FIG. 4A, a plurality of annular skin adhering members 101 are bonded to a first board 1, a solution of the electrolyte is poured into the upper portion of the openings 102 of the skin adhering members 101, and is hardened, whereby the side face 100A of the electrolyte 100 may be fixed to the side wall 102A of the opening 102.

The first board 1 corresponds to the protection sheet 106 of the living body leading electrode in accordance with the first embodiment as shown in FIG. 2A.

To this first board 1, a plurality of, for example, five annular skin adhering members 101 are bonded, a solution of the electrolyte 100 is poured into an upper portion of the openings 102, and is hardened.

As aforementioned, the electrolyte 100 is broadly divided into an electrolyte in a sol state and an electrolyte in a gel state.

The electrolyte in a sol state, as is well known, is taken as an example from an electrolyte having sodium chloride and a non-ion surface active agent for its main ingredient, and an electrolyte having potassium chloride and sodium chloride for its main ingredient, etc.

The electrolyte in a gel state, as is well known, is taken as an example from Karaya gum, acrylic gel, and urethanic gel, etc.

Karaya gum has the characteristics of sticky liquid taken from a tree trunk produced at a dry highland zone in India, which Karaya gum has glycerine, water, and potassium persulfate, etc. except for Karaya gum for its main ingredient.

Acrylic gel has acrylic acid, vinyl pyrrolidine, glycerine, water, and potassium persulfate, etc. for its main ingredient.

Urethanic gel has isocyanate, and polyole for its main ingredient.

In the first step, a solution of an electrolyte in a gel state of these above electrolytes is poured into the upper portions of the openings 102 formed on the skin adhering members 101 with a pouring means 30 of a dispenser, etc. as mentioned below with respect to FIG. 5B.

Next, the poured solution of electrolyte 100 is hardened.

Examples of means for hardening are as follows.

In case of Karaya gum, there is a means for hardening in the form of an electrolyte in a gel state having Karaya gum, glycerine, water, and potassium persulfate, etc. as its main ingredient, by heating it at 75° C.

In case of acrylic gel, there is a means for hardening in the form of an electrolyte in a gel state having acrylic acid, vinyl pyrrolidine, glycerine, water, and potassium persulfate, etc. as its main ingredient, by irradiating ultraviolet rays to it, for example, with a GE360nM lamp (Trademark of a lamp made by General Electric Company of U.S.A.).

In this case, it is preferable that ultraviolet rays are irradiated for four minutes in an atmosphere of nitrogen, and that light beginning medicine (for example, benzoylmethylchetal) or heat beginning medicine (for example, benzoyl peroxide) is used.

Moreover, in case of urethanic gel, there is a means for hardening in the form of an electrolyte in a gel state having isocyanate and polyole for its main ingredient, by using a segmentation polyether urethan reaction.

With these means, the side face 100A of the electrolyte 100 may be fixed to the side wall 102A of the opening 102.

(ii) The second step (B)

In the second step (B), as shown in FIG. 4B, a plurality of electrode elements 103 are placed on a second board 2, corresponding to a plurality of electrolytes 100 on the first board 1.

In this embodiment, referring to an electrode of the carbon type as shown in FIG. 3, lead wires 104 are connected with a plurality of electrode elements 103, respectively.

The second board 2 corresponds to the electrode element supporting member 105 as shown in FIG. 2A, on which second board 2 five electrode elements 103 with lead wires 104 are placed, for example, when the number of the electrolytes 100 on the first board 1 as shown in FIG. 4A is five.

In case of producing the electrolyte 100 wherein the electrolyte 100a in a gel state and the electrolyte 100b in a sol state are laid against each other as shown in FIG. 2D, a solution of the electrolyte 100b in a sol state is poured into previously from the upper portion of the electrode element 103 with the lead wire 104.

(iii) The third step (C)

In the third step (C), as shown in FIG. 4C, opposing the side of the first board 1 where the skin adhering members 101 and the electrolytes 100 are placed, and the side of the second board 2 where the electrode elements 103 are placed, thereafter the first board 1 and the second board 2 are superposed.

The position of the electrolytes 100 on the first board 1 and the position of the corresponding electrode elements 103 on the second board 2 are equal to each other.

Hence, when the first board and the second board 2 are superposed as shown with an arrow A in FIG. 4C, a number of, for example, five in this embodiment, living body leading electrodes, having the construction as shown in FIG. 2B or as shown in FIG. 2D, may be made.

(3) The present invention

Figure 5A:
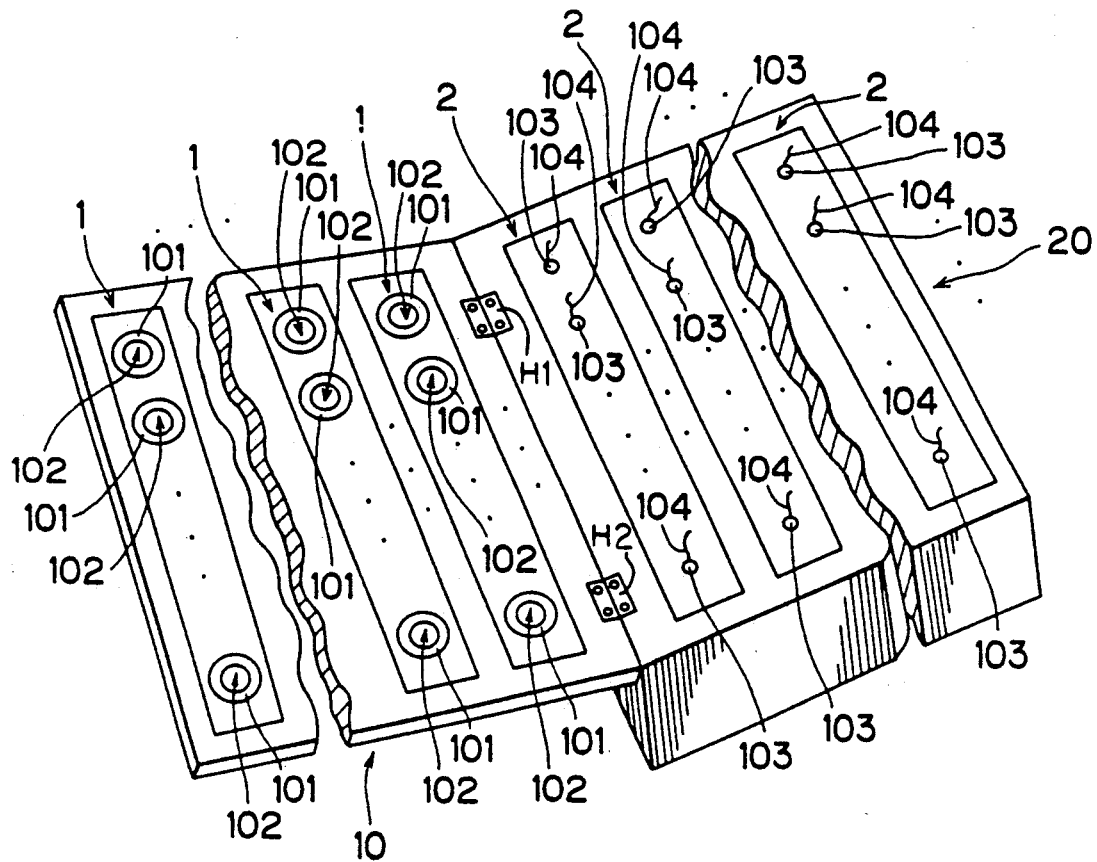
FIGS. 5A to 5C are drawings of an embodiment of an apparatus in accordance with the present invention.
Figure 5B:
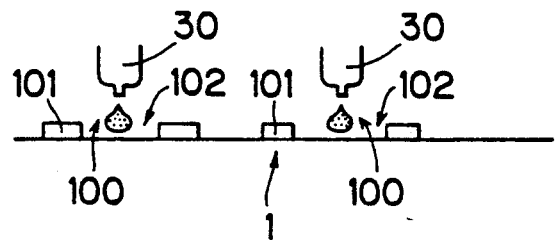
Figure 5C:
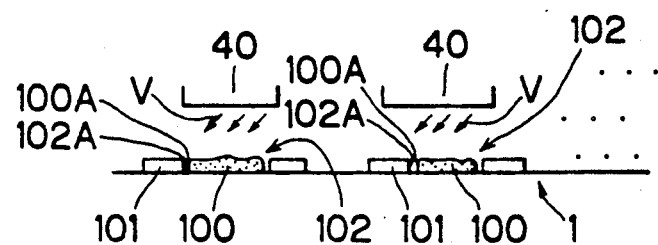

FIGS. 5A to 5C are drawings of an embodiment of an apparatus in accordance with the present invention, wherein reference numeral 10 shows a first substrate, 20 a second substrate, 30 a pouring means, and 40 a hardening means.

The first substrate 10 has a rectangular form, to which first substrate 10 a plurality of first boards 1 are fixed in many rows, for example, in five rows, to which first boards 1, a plurality of, for example, five skin adhering members 101 with openings 102 are bonded.

The second substrate 20 has the form corresponding to the first substrate 10, to which second substrate 20 second boards 2 are fixed in many rows, for example, in five rows, corresponding to the first boards 1, to which second boards 2 a plurality of, for example, five of the electrode elements 103 are placed.

In this embodiment, referring to an electrode of the carbon type as shown in FIG. 3, lead wires 104 are connected with five electrode elements 103, respectively.

The pouring means 30 may be formed, for example, by a dispenser as shown in FIG. 5B, which pouring means 30 is an apparatus for pouring a solution of the electrolytes 100 into the upper portion of the openings 102 formed on the skin adhering members 101 bonded to first boards 1 which in turn sit on the first substrate 10.

The hardening means 40 is an apparatus for hardening the electrolyte 100 poured into the opening 102, thereby fixing the side face 100A of the electrolyte 100 to the side wall 102A of the opening 102, as shown in FIG. 5C.

As an example of the hardening means 40, there is taken an apparatus for irradiating ultraviolet rays V, by arranging a plurality of GE360nM lamps (Trademark of a lamp made by General Electric Company of U.S.A.), as mentioned in the second embodiment.

Moreover, the first substrate 10 and the second substrate 20 are combined together pivotally by using hinges H1 and H2 as shown in FIG. 5A, both of which substrate 10 and 20 may be superposed on each other.

According to this apparatus for producing the living body leading electrode, a solution of the electrolytes 100 of acrylic gel, etc. is poured, with the pouring means 30 (see FIG. 5B), into the upper portions of the openings 102 formed on the skin adhering members 101 bonded to first boards 1 which in turn sit on the first substrate 10, which electrolyte 100 is hardened by irradiating ultraviolet rays V, with the hardening means 40 (see FIG. 5C), thereby the side face 100A of the electrolyte 100 is fixed to the side wall 102A of the opening 102, and the first substrate 10 and the second substrate 20 are superposed on each other, to which the second substrate 20 and second boards 2, where a plurality of electrode elements 103 with lead wires 104 are placed, have already been fixed in a plurality of rows.

The result is that the living body leading electrode as shown in FIGS. 2A to 2D may be produced.

In embodiments of the present invention, an electrode of the carbon type is referred to as shown in FIG. 3.

However, since the present invention is not restricted to the above embodiments, it follows that the present invention is also applicable to an electrode of the hook type where a hook connector with a lead wire is engaged with another connector projecting from the electrode element 103.

According to the present invention, there is provided with a living body leading electrode as shown in FIGS. 2A to 2D and FIG. 3, a method for producing it as shown in FIGS. 4A to 4C, and an apparatus for producing it as shown in FIGS. 5A to 5C.

(1) According to the living body leading electrode (see FIGS. 2A to 2D and FIG. 3), the side face 100A of the electrolyte 100 is fixed to the side wall 102A of the opening 102.

Hence, as shown with a thick line F in FIG. 2C, the electrolyte 100 is contacted with the opening 102, which electrolyte 100 is integrated with the skin adhering member 101.

Accordingly, when the living body leading electrode in accordance with the present invention is removed from the breast, the electrolyte 100 is removed together with the skin adhering member 101, such that the electrolyte 100 does not remain on the breast.

(2) According to the method and the apparatus (see FIGS. 4A to 4C and FIGS. 5A to 5C), a solution of the electrolytes 100 is made to be poured into the upper portion of the openings 102 of the skin adhering members 101, and is hardened, whereby the side face 100A of the electrolyte 100 may be fixed to the side wall 102A of the opening 102.

That is to say, there is the characteristic in that a solution of the electrolyte 100 is directly poured into the opening 102, thereafter it is hardened.

Hence, a process for punching the electrolyte is unnecessary, which process results in a great loss, and it is unnecessary to add the process wherein the electrolyte must be picked up one by one with a pincette.

Accordingly, the efficiency of producing the electrode is higher.

Therefore, the present invention has the effect to prevent the electrolyte from being separated in case of removing the living body leading electrode from the breast, and to elevate the efficiency of producing the living body leading electrode.

Moreover, the present invention has the additional effect to provide the electrolyte 100 in which an electrolyte 100a in a gel state and an electrolyte 100b in a sol state are laid on each other as shown in FIG. 2D, and to produce more cheaply the living body leading electrode.

What is claimed is:

1. An apparatus for producing living body leading electrodes, said apparatus comprising:
   a first substrate having a plurality of first boards fixed thereto and arranged in a plurality of rows disposed substantially parallel to each other, said first boards each having a plurality of annular skin adhering members bonded thereto, thereby to define a plurality of openings formed by inner, side wall portions of said annular skin adhering members, and by a surface of a corresponding first board;
   a second substrate having a plurality of second boards fixed thereto and arranged in a plurality of rows disposed substantially parallel to each other corresponding to said plurality of rows of said first boards, said second boards each having a plurality of electrode elements disposed thereon;
   pouring means for pouring a solution of electrolyte into an upper portion of each of said openings thereby to fill said openings such that side faces of said electrolyte touch the side wall portions of said openings;
   hardening means for hardening said poured solution of electrolyte, thereby to fix the side faces of said electrolyte to the side wall portions of said openings;
   wherein said first substrate and said second substrate are operative to be superposed on each other, thereby to respectively join each of said electrode elements together with a corresponding one of said hardened electrolytes fixed to said annular skin adhering members.

2. The apparatus according to claim 1, wherein said pouring means pours a solution of a first electrolyte in a gel state into the upper portions of said openings, and pours a solution of a second electrolyte in a sol state.

3. The apparatus according to claim 1, further comprising hinges for pivotally joining together said first and second substrates along adjacent edges thereof.

* * * * *